United States Patent
Singh et al.

(10) Patent No.: US 10,227,317 B2
(45) Date of Patent: Mar. 12, 2019

(54) PROCESS FOR THE PREPARATION OF VORTIOXETINE

(71) Applicant: Lupin Limited, Mumbai (IN)

(72) Inventors: Girij Pal Singh, Pune (IN); Dhananjai Srivastava, Pune (IN); Paramvir Bhadwal, Pune (IN); Inamus Saqlain Ansari, Pune (IN); Nilesh Shashikant Bhawsar, Pune (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 15/552,985

(22) PCT Filed: Feb. 24, 2016

(86) PCT No.: PCT/IB2016/050992
§ 371 (c)(1),
(2) Date: Aug. 23, 2017

(87) PCT Pub. No.: WO2016/135636
PCT Pub. Date: Sep. 1, 2016

(65) Prior Publication Data
US 2018/0030008 A1 Feb. 1, 2018

(30) Foreign Application Priority Data
Feb. 25, 2015 (IN) .......................... 626/MUM/2015
May 26, 2015 (IN) .......................... 2052/MUM/2015

(51) Int. Cl.
*C07D 295/096* (2006.01)
*C07C 323/09* (2006.01)
*C07C 327/22* (2006.01)
*C07D 295/205* (2006.01)

(52) U.S. Cl.
CPC ........ *C07D 295/096* (2013.01); *C07C 323/09* (2013.01); *C07C 327/22* (2013.01); *C07D 295/205* (2013.01); *C07B 2200/13* (2013.01)

(58) Field of Classification Search
CPC ............ C07D 295/096; C07D 295/205; C07C 323/09; C07C 327/22
USPC ....................................................... 544/395
See application file for complete search history.

(56) References Cited

U.S. PATENT DOCUMENTS 3,250,812 A    5/1966 Gilbert

FOREIGN PATENT DOCUMENTS

| DE | 26 44 591 | 2/1976 |
| WO | 2006/046914 A1 | 5/2006 |
| WO | 2007/144005 A1 | 12/2007 |
| WO | 2014/191548 A1 | 12/2014 |

OTHER PUBLICATIONS

Canadian Journal of Chemistry, vol. 58, No. 24, Electrophilic Additions to Allenes. VI. The Role of Steric Versus Electronic Effects in the Reactions of ARenesulphenyl Halides with Allenes, Dated Dec. 15, 1980.
PCT Search Report & Written Opinion dated Aug. 9, 2016, Application No. PCT/IB2016/050992.
J. Org. Chem., Formylation of Aromatic Compounds with CO in HSO3F-SbF5 Under Atmospheric Pressure, 1992.
J. Org. Chem., Enantioselective Inclusion of Methyl Phenyl Sulfoxides and Benzyl Methyl Sulfoxides by R-Phenylglycyl-R-Phenylglycine and the Crystal Structures of the Inclusion Cavities, 2000.
Journal of the American Chemical Society, Dated Sep. 4, 1996, A Practical Method for the Synthesis of Sialyl a-Glycosides.
Journal of Medicinal Chemistry, 2011, Discovery of 1-[2-(2,4-Dimethylphenylsulfanyl)phenyl]piperazine (Lu AA21004): A Novel Multimodal Compound for the Treatment of Major Depressive Disorder.
Angewandte Communications, Double Heteroatom Functionalization of Arenes Using Benzyne Three-Component Coupling, 2015.
Organic Letters, vol. 9, No. 12, Highly Enantioselective Oxidation of Sulfides to Sulfoxides by a New Oxaziridinium Salt, 2007.
Journal Homepage, Protonation of Alkyl Aryl Sulphides in Antimony Pentafluoride-Fluoro-sulphonic Acid Solution, 1981.
Laboratory of Organic Chemistry, Xanthydrol as a Reagent for the Identification of Sulfonamides, dated Jul. 21, 1943.

*Primary Examiner* — Kahsay Habte
(74) *Attorney, Agent, or Firm* — The Dobrusin Law Firm, PC

(57) ABSTRACT

Disclosed herein a process for the isolation of intermediate of Vortioxetine in a solid state form and an improved, commercially viable and industrially advantageous process for the preparation of vortioxetine or a pharmaceutically acceptable salt thereof, in high yield and purity.

7 Claims, 1 Drawing Sheet

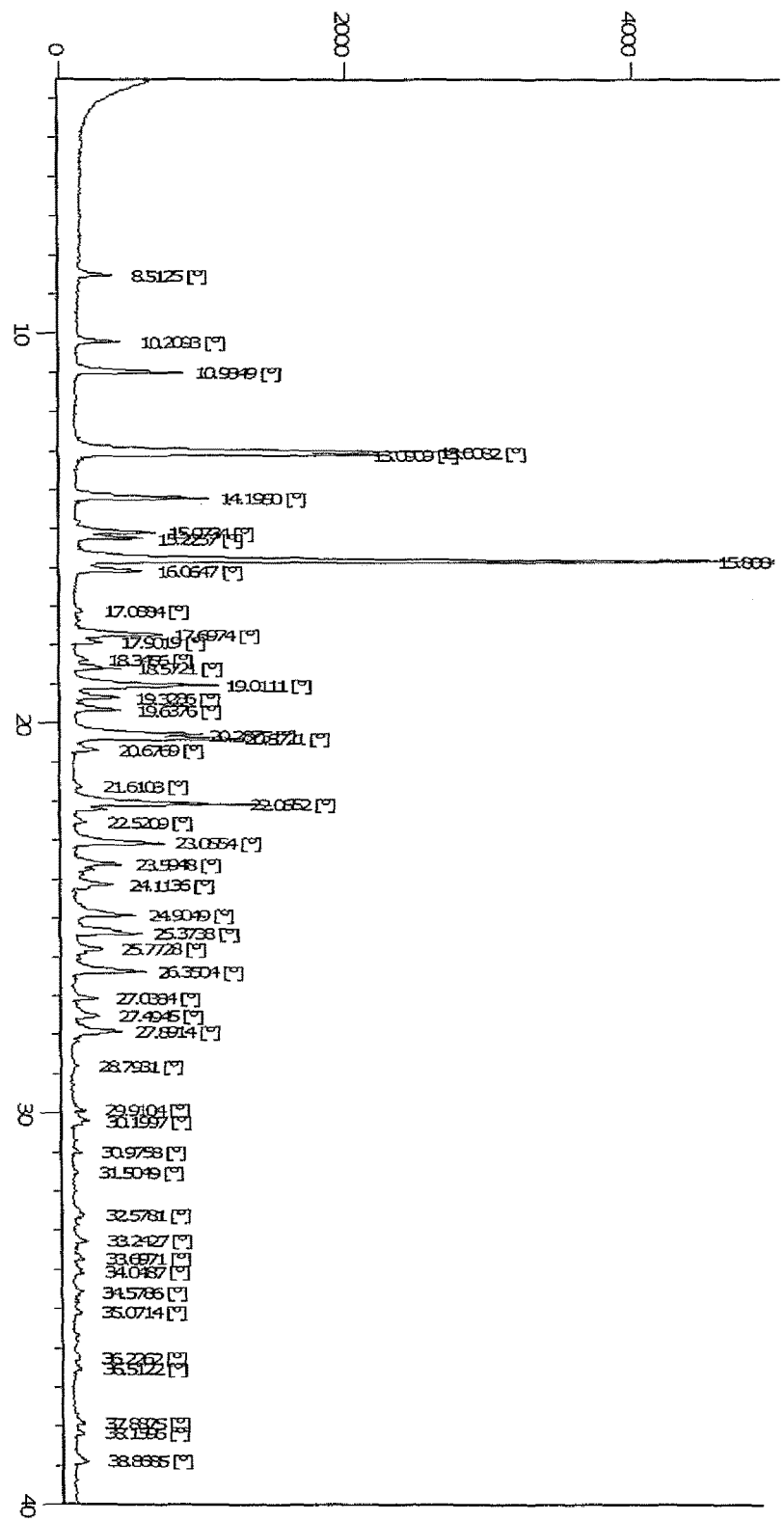

PROCESS FOR THE PREPARATION OF VORTIOXETINE

FIELD OF THE INVENTION

The present invention provides a process for the isolation of intermediate of Vortioxetine in a solid state form and a novel process for the preparation of vortioxetine or a pharmaceutically acceptable salt thereof.

BACKGROUND OF THE INVENTION

Vortioxetine is chemically known as 1-[2-(2, 4-Dimethylphenylsulfanyl)-phenyl]-piperazine. Vortioxetine is a new antidepressant that has been approved for the treatment of Major Depressive Disorder (MDD) by FDA and EMEA under the trade name of Brintellix®.

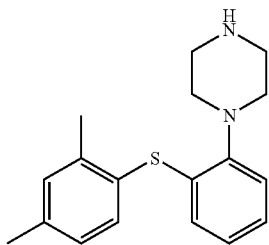

IA

It was intended to have combined effects on multiple 5-HT receptors and on the serotonin transporter. The combination of 5-HT3 and 5-HT7 receptor antagonism, 5-HT1B receptor partial agonism, 5-HT1A receptor agonism, and serotonin transporter inhibition have been shown in recombinant cell lines.

PCT application WO2003029232 by Lundbeck discloses compounds which are useful in the treatment of an affective disorder, including depression, anxiety disorder. The preparation of vortioxetine is described in example 1e with 17% yield.

PCT application WO2007144005 by Lundbeck discloses crystalline vortioxetine and its pharmaceutically acceptable salts in its crystalline form and various methods for the preparation of Vortioxetine by using compounds A, B and C in presence of base and Pd catalyst.

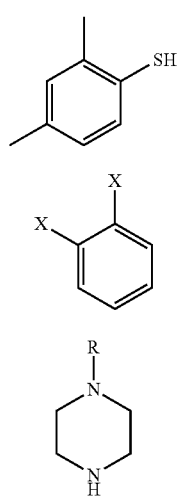

Wherein X=Cl, Br and I, R=H or protecting group;

PCT application WO2013102573 by Lundbeck claims a process for the preparation of vortioxetine by using compound I, II and III

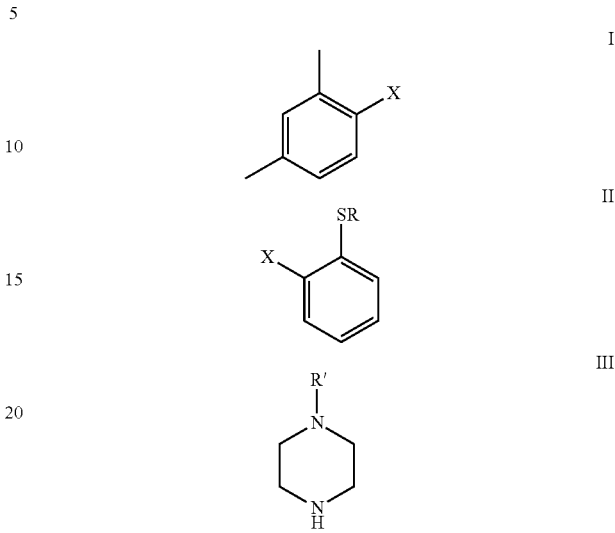

wherein X=Halogen, R=H or metal ion, R'=Protecting group.

PCT application WO2014161976 by Lek pharmaceuticals claims novel intermediates of the formulae

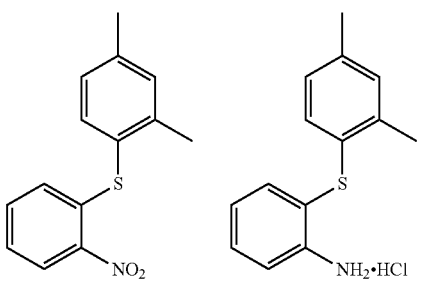

and their use in preparation of vortioxetine.

PCT application WO2014191548 by Lek pharmaceuticals claims novel intermediates of the formula

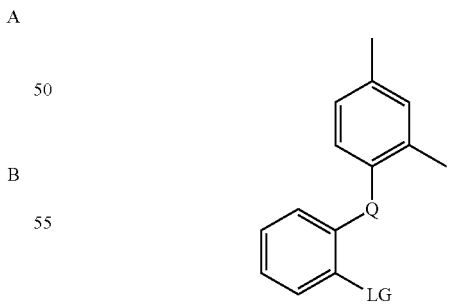

wherein Q=S, SO or SO2; and LG=Leaving group;
and their use in preparation of Vortioxetine without using Pd catalyst.

Though the process of manufacturing of Vortioxetine has been described in various applications, the present process is a novel approach by the inventors towards attaining significant cost effective method by using different starting material to give better yield.

SUMMARY OF THE INVENTION

In one aspect, the present invention provides process for the preparation of Vortioxetine or a pharmaceutically acceptable salt thereof.

In another aspect, the present invention provides process for the preparation of Vortioxetine or a pharmaceutically acceptable salt thereof by using following intermediates:

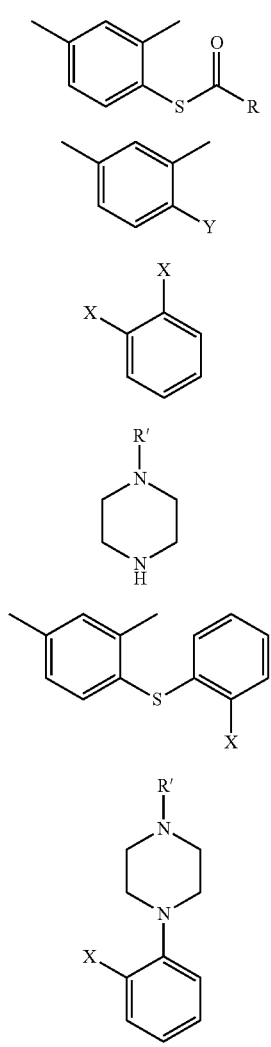

wherein X=a leaving group; R=hydrogen, alkyl or an aromatic group; R'=hydrogen or a protecting group; Y is selected from the group consisting of —SR",

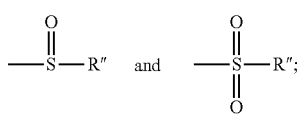

and R" is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide;

In another aspect, the present invention provides a process for the preparation of Vortioxetine or a pharmaceutically acceptable salt thereof by using following intermediates:

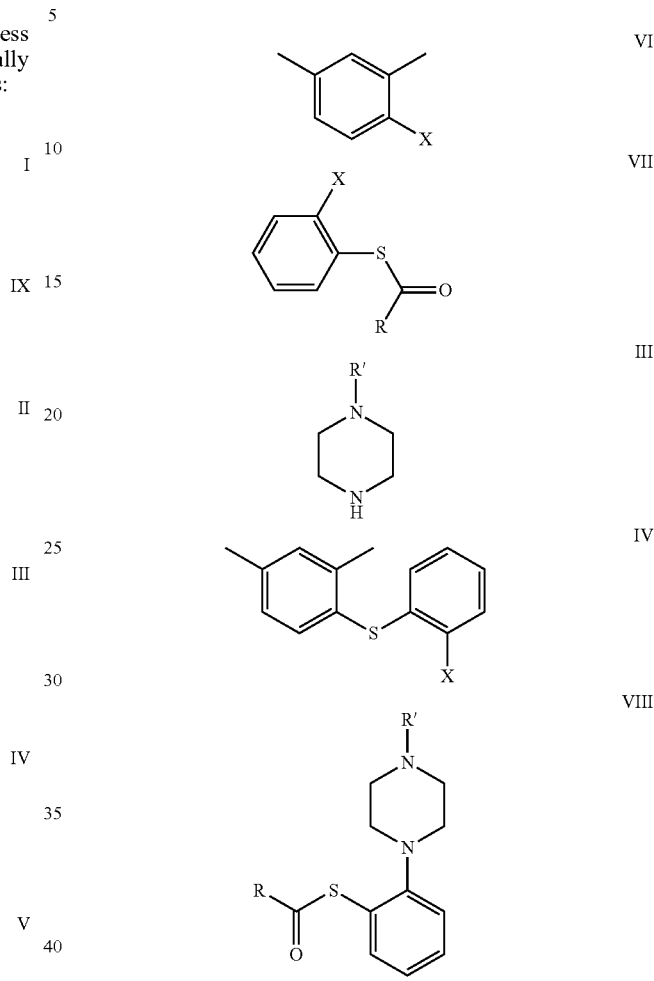

wherein X=a leaving group; R=Hydrogen, alkyl or an aromatic group; and R'=hydrogen or a protecting group.

In another aspect, the present invention provides a process for the preparation of vortioxetine hydrobromide as shown in Scheme I:

Scheme I

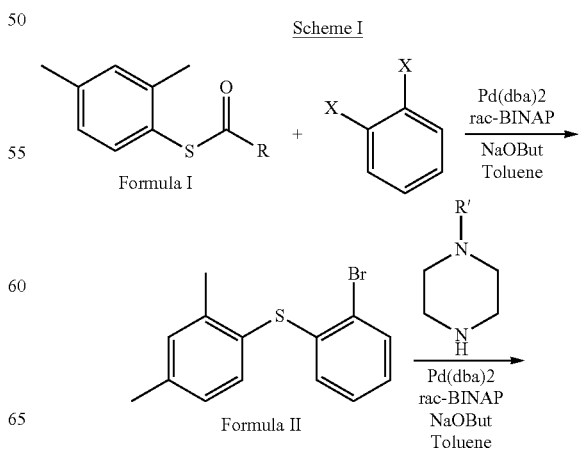

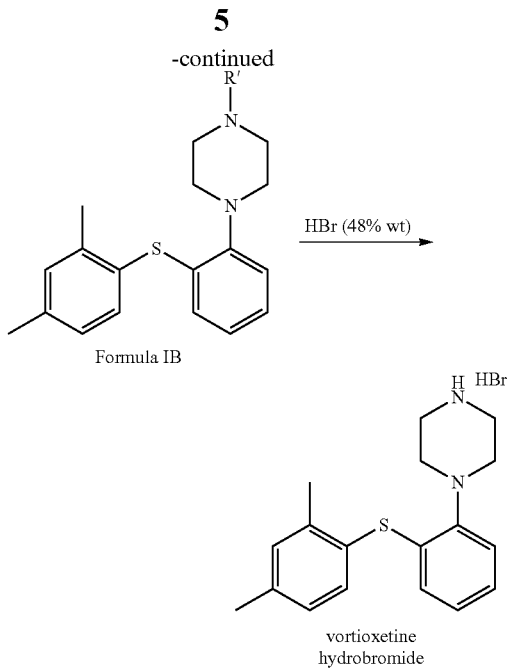

Formula IB vortioxetine hydrobromide

In another aspect, the invention provides compound of formula IC in solid state form.

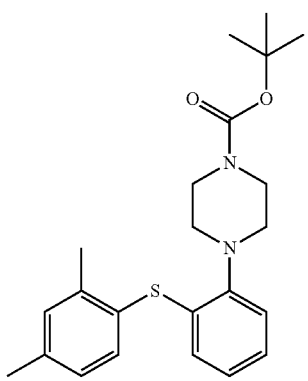

Formula IC

In another aspect, the invention provides a process for the isolation of compound of formula IC in solid state form.

In another aspect, the invention provides a crystalline form of compound of formula IC with XPRD.

In another aspect, the invention provides a process for the preparation of compound of formula I.

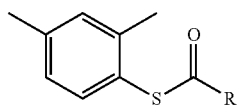

I

DESCRIPTION OF DRAWINGS

FIG. 1: illustrates X-ray powder diffraction pattern of crystalline form of compound of Formula IC.

DETAIL DESCRIPTION OF THE INVENTION

The term "protecting group" is used herein to describe groups present in the textbook protecting groups in organic synthesis T. W. Greene and P. G. M. Wuts, Willey Interscience, (1991) ISBN 0471623016.

The term "leaving group" represents an atom or group (charged or uncharged) that becomes detached from an atom in what is considered to be the residual or main part of the substrate in a specified reaction. More particularly, as used herein the "leaving group" represents an atom or group which can be substituted in a reaction of nucleophilic aromatic substitution. Examples of leaving groups as used herein include, but are not limited to, F, Cl, Br, hydroxy, silyl, mesyl, tosyl, OTf (i.e. triflate), grignard reagent, phosphate and borate.

In one embodiment, the present invention provides a process for the preparation of Vortioxetine or a pharmaceutically acceptable salt thereof by the following methods:

Method A:

A process for the preparation of Vortioxetine or a pharmaceutically acceptable salt thereof comprising:

i) reacting a compound of formula I

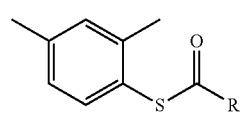

wherein R=hydrogen, alkyl or an aromatic group; with a compound of formula II:

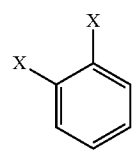

wherein each X independently=a leaving group; in the presence of a solvent, a base and optionally in the presence of a palladium source to obtain a compound of formula IV:

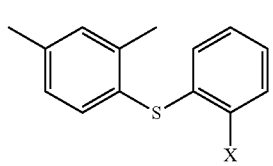

ii) reacting the compound of formula IV with a compound of formula III:

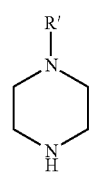

wherein R'=hydrogen or a protecting group; in the presence of a solvent, a base and optionally in the presence of a palladium source and followed by a de-protection step as required when the optionally protected compound of formula III is used, to obtain vortioxetine or a pharmaceutically acceptable thereof; or Method B:

A process for the preparation of vortioxetine or a pharmaceutically acceptable salt thereof comprising:

i) reacting a compound of formula II:

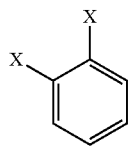

II wherein each X independently=a leaving group; with a compound of formula III:

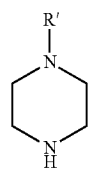

III wherein R'=hydrogen or a protecting group; in the presence of a solvent, a base and optionally in the presence of a palladium source to obtain compound of formula V;

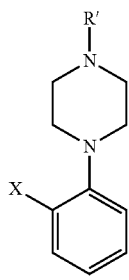

V ii) reacting the compound of formula V with a compound of formula I:

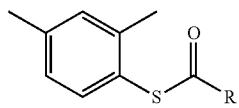

I wherein R=hydrogen, alkyl or an aromatic group; in the presence of a solvent, a base and optionally in the presence of a palladium source and followed by a de-protection step as required when the optionally protected compound of formula III is used, to obtain vortioxetine or a pharmaceutically acceptable salt thereof.

Method C:

A process for the preparation of vortioxetine or a pharmaceutically acceptable salt thereof comprising:

i) reacting a compound of formula IX

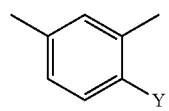

IX wherein Y is selected from the group consisting of —SR″,

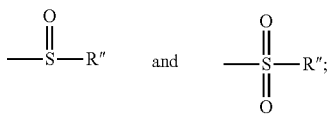

and R″ is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide; with a compound of formula II:

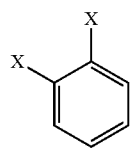

II wherein each X independently=a leaving group; in the presence of solvent, a base and optionally in the presence of a palladium source to obtain a compound of formula IV:

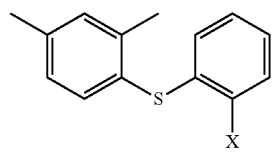

IV ii) reacting the compound of formula IV with a compound of formula III:

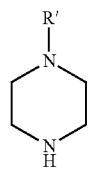

III wherein R'=hydrogen or a protecting group; in the presence of a solvent, a base and optionally in the presence of a palladium source and followed by a de-protection step as required when the optionally protected compound of formula III is used, to obtain vortioxetine or a pharmaceutically acceptable salt thereof;

Method D:

A process for the preparation of vortioxetine or a pharmaceutically acceptable salt thereof comprising:

i) reacting a compound of formula II

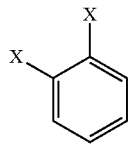
II wherein each X independently=a leaving group; with a compound of formula III;

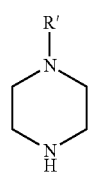
III wherein R'=hydrogen or a protecting group; in the presence of a solvent, a base and optionally in the presence of a palladium source to obtain a compound of formula V;

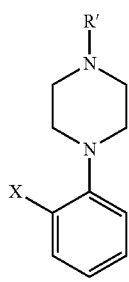
V ii) reacting the compound of formula V with a compound of formula IX;

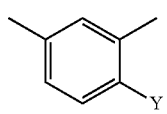
IX wherein Y is as described above; in the presence of a solvent, a base and optionally in the presence of a palladium source and followed by a de-protection step as required when the optionally protected compound of formula III is used, to obtain vortioxetine or a pharmaceutically acceptable salt thereof.

Method E:
A process for the preparation of vortioxetine or a pharmaceutically acceptable salt thereof comprising:
i) reacting a compound of formula VI

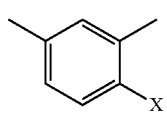
VI wherein X=a leaving group; with a compound of formula VII:

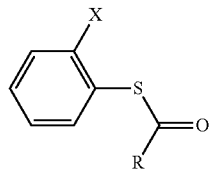
VII wherein X=a leaving group; R=hydrogen, alkyl or aromatic group; in the presence of a solvent, a base and optionally in the presence of a palladium source to obtain a compound of formula IV:

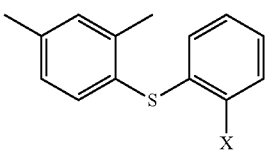
IV ii) reacting the compound of formula IV with a compound of formula III:

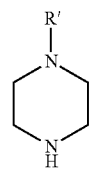
III wherein R'=hydrogen or a protecting group; in the presence of a solvent, a base and optionally in the presence of a palladium source and followed by a de-protection step as required when the optionally protected compound of formula III is used, to obtain vortioxetine or a pharmaceutically acceptable salt thereof; or Method F:
A process for the preparation of vortioxetine or a pharmaceutically acceptable salt thereof comprising:
i) reacting a compound of formula VII:

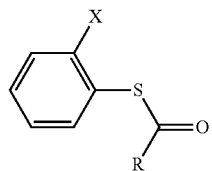
VII wherein X=a leaving group; R=hydrogen, alkyl or an aromatic group; with a compound of formula III:

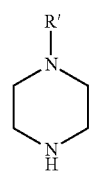
III wherein R'=hydrogen or a protecting group; in the presence of a solvent, a base and optionally in the presence of a palladium source to obtain a compound of formula VIII:

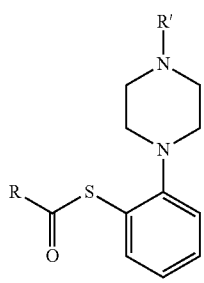

VIII ii) reacting the compound of formula VIII with a compound of formula VI:

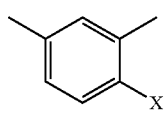

VI wherein X=a leaving group; in the presence of a solvent, a base and optionally in the presence of a palladium source and followed by a de-protection step as required when the optionally protected compound of formula III is used, to obtain vortioxetine or a pharmaceutically acceptable salt thereof.

In another embodiment, the invention provides a process for the preparation of vortioxetine or a pharmaceutically acceptable salt thereof by using following intermediate:

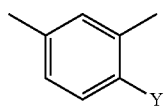

IX wherein Y is selected from the group consisting of —SR",

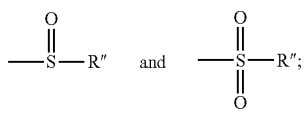

and R" is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide;

Exemplary solvents used herein include, but are not limited to, a chlorinated hydrocarbon, a hydrocarbon, a ketone, an ester, an ether, a nitrile, a polar aprotic solvent, and mixtures thereof. The term solvent also includes mixtures of solvents.

In one embodiment, the solvent is selected from the group consisting of methylene chloride, ethylene dichloride, chloroform, carbon tetrachloride, n-pentane, n-hexane, n-heptane, cyclohexane, toluene, xylene, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, tetrahydrofuran, dioxane, diethyl ether, diisopropyl ether, monoglyme, diglyme, N,N-dimethylformamide, N,N-dimethylacetamide, dimethylsulfoxide, and mixtures thereof. More specifically, the solvent is toluene.

The palladium source used herein includes without limitation, a palladium catalyst and a phosphine ligand. Useful palladium catalysts include palladium in different oxidations states, such as e.g. 0 and II. Examples of palladium catalyst which may be used in the process of the present invention include, but are not limited to, Tris(dibenzylideneacetone) dipalladium ($Pd_2(dba)_3$), Bis(dibenzylideneacetone)palladium ($Pd(dba)_2$) and Palladium(II) acetate ($Pd(OAc)_2$). In one embodiment, the palladium catalyst is $Pd(dba)_2$.

Numerous phosphine ligands are known, both monodentate and bidentate. Useful phosphine ligands include, without limitation, racemic 2,2'-bis-diphenylphosphanyl-[1,1'] binaphtalenyl(rac-BINAP), 1,1'-bis(diphenylphosphino) ferrocene (DPPF), bis-(2-diphenylphosphinophenyl)ether (DPEphos), tri-t-butyl phosphine (Fu's salt), biphenyl-2-yl-di-t-butyl-phosphine, biphenyl-2-yl-dicyclohexyl-phosphine, (2'-dicyclohexylphosphanyl-biphenyl-2-yl)-dimethyl-amine, [2'-(di-t-butyl-phosphanyl)-biphenyl-2-yl]-dimethyl-amine, and dicyclohexyl-(2',4',6'-tri-propyl-biphenyl-2-yl)-phosphane Moreover, carbene ligands, such as e.g. 1,3-bis-(2,6-di-isopropyl-phenyl)-3H-imidazol-1-ium; chloride may be used instead of phosphine ligands. In one embodiment, the phosphine ligand is rac-BINAP, DPPF or DPEphos, and in particular rac-BINAP.

The base used herein includes without limitation, an organic or an inorganic base. Base is added to the reaction mixture to increase pH. In one embodiment, the base is selected from the group consisting of NaOt-Bu, KOt-Bu and Cs2CO3. Organic bases, such as 1,8-diazabicyclo[5.4.0]undec-7-ene (DBU) and 1,4-diazabicyclo[2.2.2]octane (DABCO) may be used as well. In one embodiment, the base is Nao(t-Bu). Typically, the base is added in an amount around 1-5 equivalents, such as 1-3 equivalents, such as 2-3 equivalents.

The deprotection can be performed by using an aqueous acid, such as HCl, HBr, $H_2SO_4$ or $H_3PO_4$, in an alcohol solvent, preferably $C_1$-$C_6$ alcohol, and more preferably methanol or ethanol.

In another embodiment, the present invention provides compound of formula IC in a solid state form.

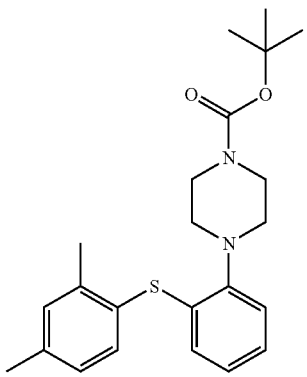

IC

The meaning of solid state form includes both crystalline and amorphous form.

In another embodiment, the present invention provides a process for the isolation of compound of formula IC in a solid state form comprising:

a) dissolving oily residue of tert-butyl 4-(2-((2,4-dimethylphenyl) thio) phenyl) piperazine-1-carboxylate in a solvent or in mixture of solvents;
b) optionally cooling above solution; and
c) isolating solid state form of tert-butyl 4-(2-((2,4-dimethylphenyl)thio)phenyl) piperazine-1-carboxylate.

The solvent used for step [i] is selected from but not limited to methanol, ethanol, n-propanol, isopropanol, acetone, propanone, butanone, water, ethyl acetate, acetonitrile, n pentane, hexane, n heptane, toluene, benzene, ethyl methyl ketone, diethyl ether, ethyl methyl ether, diisopropyl ether, cyclic ethers such as tetrahydrofuran, dioxane and mixtures thereof; most preferably n heptane.

The temperature used for the dissolution oily residue of tert-butyl 4-(2-((2,4-dimethylphenyl)thio)phenyl)piperazine-1-carboxylate is carried out at a temperature of 10 to 80° C., most preferably at 10 to 30° C.

Solid form of compound of formula IC was isolated by using conventional techniques known in prior art such as filtration, centrifugation etc.

In another embodiment, the invention provides a crystalline form of compound of formula IC, which is characterized by XRPD (X-ray powder diffractogram) which comprises of peaks expressed as 2θ at 10.21, 10.98, 13.00, 13.09, 14.20, 15.07, 15.22, 15.81, 16.06, 17.69, 19.01, 20.28, 22.05, 23.05, and 26.35±0.2 degrees. The XRPD of crystalline form of compound IC is depicted in FIG. 1.

In another embodiment, the process for the preparation of a compound of formula I:

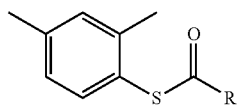

I comprises reacting 2,4 dimethyl thiophenol with an acyl chloride of formula ID

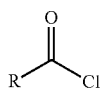

ID wherein R=hydrogen, alkyl or an aromatic group; in the presence of a base.

The base used for the reaction is selected from the group consisting of ammonia, methylamine, triethylamine, N,N diethyl amine, N,N-dimethylethylamine, 4-Dimethylaminopyridine, aniline, and pyridine. Most preferably base used for the reaction is pyridine.

In another embodiment, the present invention provides following intermediate compounds of vortioxetine or a pharmaceutically acceptable salt thereof

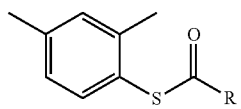

I

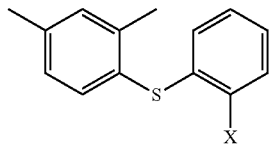

IV

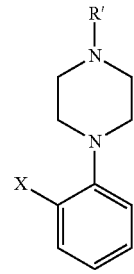

V

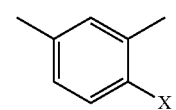

VI

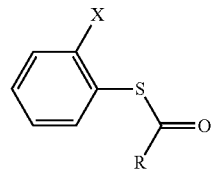

VII

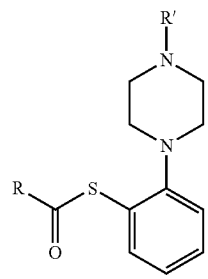

VIII

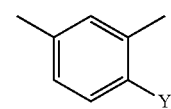

IX

Wherein X=a leaving group provided that X is not halogen in formula IV, V, VI and VII; R=hydrogen, alkyl or an aromatic group; R'=hydrogen or a protecting group; Y is selected from the group consisting of —SR″,

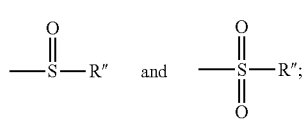

and R″ is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide;

EXAMPLES

Example 1

Preparation of S-(2,4-dimethylphenyl) ethanethioate 100 g of 2,4 dimethyl thiophenol was suspended in 500 ml of dichloromethane and added 94 gm of pyridine at 25° C. Reaction mixture was cooled to 5-10° C. and then drop wise added acetyl chloride (64 gm, 0.815 mole). Resulting reaction mixture was heated at 5-15° C. for 1 hr. RM was monitored by HPLC. When reaction was completed cooled to RT, added water and stirred for 10-20 mins. Desired product was extracted with ethyl acetate twice. Combined organic layer was washed with water, brine, dried over sodium sulfate and concentrated under reduced pressure to give oily mass as desired product (130 gm, 100%).

Example 2

Preparation of (2-bromophenyl)(2,4-dimethylphenyl) sulfane 100 g of S-(2,4-dimethylphenyl) ethanethioate was suspended in 500 ml of degassed toluene. Then added Pd(dba)$_2$ (3.25 gm, 0.006 mole), rac-BINAP (6.4 gm, 0.01 mole), and sodium tert-butoxide (62.5 g, 0.65 mole) under nitrogen purging. Reaction mixture was heated to 45-55° C. and then added 2-iodo-1-bromo benzene (165 gm, 0.583 mole). Reaction mixture was stirred at 90-100° C. for 3 hrs under nitrogen atmosphere. After completion of the reaction, it was cooled to room temperature and added 400 ml of water, and allowed to stir for 15-20 mins. Reaction mixture was allowed to settled and organic layer was separated and concentrated under reduced pressure to give thick viscous oil to give desired product (2-bromophenyl)(2,4-dimethylphenyl) sulfane (162 gm, 100%)

Example 3

Preparation of tert-butyl 4-(2-((2,4-dimethylphenyl)thio)phenyl)piperazine-1-carboxylate Step A (2-bromophenyl)(2,4-dimethylphenyl)sulfane (211 gm, 0.722 mole), N-BOC piperazine (161.54 gm, 0.866 mole), Pd(dba)$_2$ (8.3 gm, 0.014 mole) and rac-BINAP (17.98 gm, 0.028 mole) were charged in 1055 ml toluene. Reaction mixture was purged with nitrogen and added sodium tert-butoxide (138.8 gm, 1.44 mole), then reaction mixture was heated at 100-110° C. for 2-4 hrs. The reaction mixture was cooled to RT and 420 ml of water was added. Organic layer was separated and distilled off the solvents under reduced pressure at 50° C. to give oily residue (560 gm).

Step B

To the RB flask containing oily residue was added n-Heptane (2.1 L), stirred, cooled to 5-10° C., filtered through celite bed and washed the bed with n-Heptane (200 mL). Distilled off the solvents under reduced pressure at 50° C. Again n-Heptane (2.1 L) was added, stirred, filtered through celite bed, washed the bed with n-Heptane (100 mL). Distilled off the solvents under reduced pressure at 50° C. and methanol was added (250 mL) then reaction mass was stirred, cooled at −10 to 0° C. for 3-8 hrs. Reaction mass was filtered, washed with chilled methanol (200 mL) and suck dried. Wet cake was dried under reduced pressure at 40-50° C. to get solid desired product (222 gm, 77.4%).

Example 4

Preparation of 1-(2-((2,4-dimethylphenyl)thio)phenyl)piperazine Hydrobromide (1:1)

tert-butyl 4-(2-((2,4-dimethylphenyl)thio)phenyl)piperazine-1-carboxylate (100 gm, 0.25 mole) was suspended in methanol (500 mL) Aq. HBr (47%) (100 mL) was added under stirring at 20-30° C. Reaction mass was heated and stirred at 50-60° C. for 1 hr. reaction progress was monitored by HPLC. After reaction was completed, Distilled off the solvents up to 0.5 volume, then (200 mL) of Ethyl acetate was added, chilled and stirred at RT. Reaction mixture was filtered and washed with Ethyl acetate (100 mL). Wet solid was dried under reduced pressure at 50° C. to obtain Vortioxetine Hydrobromide. Crude Vortioxetine hydrobromide was recrystallized in methanol and water to get pure Vortioxetine Hydrobromide (80 gm, 83.5%).

The invention claimed is:

1. A process for the preparation of vortioxetine of formula IA

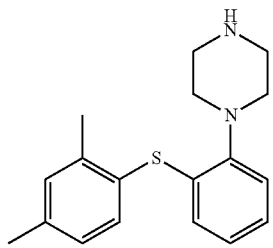

IA or a pharmaceutically acceptable salt thereof according to any one of process alternative methods A, B, C, D, E and F;

Method A:

a) reacting a compound of formula I

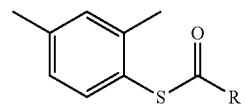

I wherein R is hydrogen, alkyl or an aromatic group; with a compound of formula II in the presence of a base, a palladium catalyst, a ligand and a solvent;

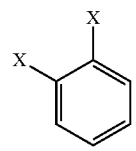

II wherein each X independently is a leaving group; to obtain a compound of formula IV;

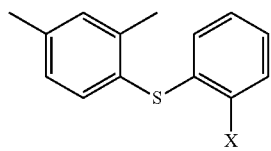

IV b) reacting the compound of formula IV with a compound of formula III in the presence of a base, a palladium catalyst, a ligand and a solvent;

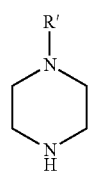

III wherein R' is hydrogen or a protecting group; to obtain a compound of formula IB;

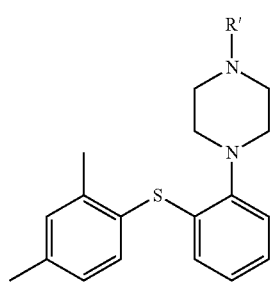

IB c) optionally the compound of formula IB is de-protected when R' is a protecting group, to obtain the compound of formula IA or a pharmaceutically acceptable salt thereof;

Method B:

a) reacting a compound of formula II

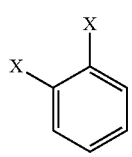

II wherein each X independently is a leaving group; with a compound of formula III in the presence of a base, a palladium catalyst, a ligand and a solvent;

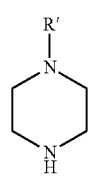

III wherein R' is hydrogen or a protecting group; to obtain a compound of formula V;

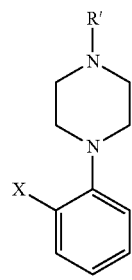

V b) reacting the compound of formula V with a compound of formula I in the presence of a base, a palladium catalyst, a ligand and a solvent;

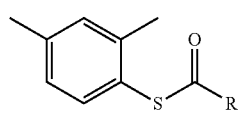

I wherein R=hydrogen, alkyl or an aromatic group; to obtain a compound of formula IB;

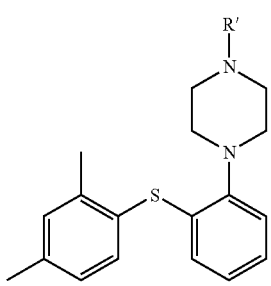

IB c) optionally the compound of formula IB is de-protected when R' is a protecting group, to obtain the compound of formula IA or a pharmaceutically acceptable salt thereof;

Method C:

a) reacting a compound of formula IX

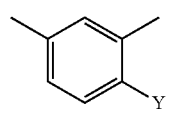

IX wherein Y is selected from the group consisting of —SR″,

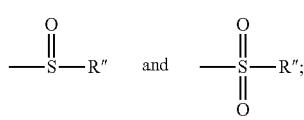

and R″ is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide; with a compound of formula II in the presence of a base, a palladium catalyst, a ligand and a solvent;

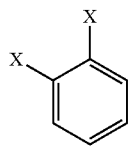

II wherein each X independently is a leaving group; to obtain a compound of formula IV;

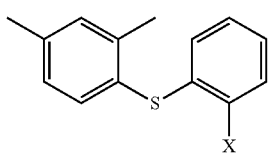

IV b) reacting the compound of formula IV with a compound of formula III in the presence of a base, a palladium catalyst, a ligand and a solvent;

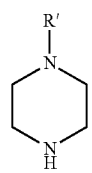

III wherein R' is hydrogen or a protecting group; to obtain a compound of formula IB;

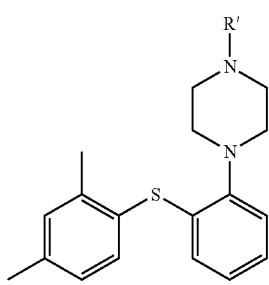

IB c) optionally the compound of formula IB is de-protected when R' is a protecting group, to obtain the compound of formula IA or a pharmaceutically acceptable salt thereof;

Method D:

a) reacting a compound of formula II

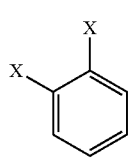

II wherein each X independently is a leaving group; with a compound of formula III in the presence of a base, a palladium catalyst, a ligand and a solvent;

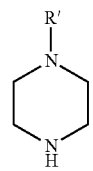

III wherein R' is hydrogen or a protecting group; to obtain a compound of formula V;

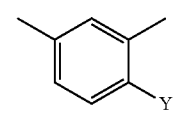

V b) reacting the compound of formula V with a compound of formula I in the presence of a base, a palladium catalyst, a ligand and a solvent;

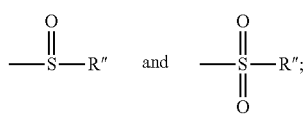

I wherein Y is selected from the group consisting of —SR", $$-\overset{\overset{O}{\|}}{\underset{}{S}}-R'' \quad \text{and} \quad -\overset{\overset{O}{\|}}{\underset{\underset{O}{\|}}{S}}-R'';$$

and R" is selected from the group consisting of alkyl, halogen, aromatic, heteroaromatic, benzoyl, benzyl, benzene sulphonate, trifluromethyl sulfinyl, acyl, hydroxy, cyano, nitro, silyl, mesyl, tosyl, trifluoromethyl sulphonyl, sulphonic acid, hydrazine, phosphate, phthalimide, and succinimide; to obtain a compound of formula IB

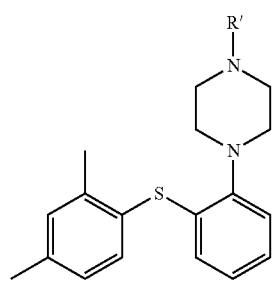

IB c) optionally the compound of formula IB is de-protected when R' is a protecting group, to obtain the compound of formula IA or a pharmaceutically acceptable salt thereof;

Method E:

a) reacting a compound of formula VI

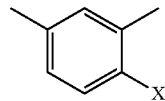

VI wherein X is a leaving group; with a compound of formula VII in the presence of a base, a palladium catalyst, a ligand and a solvent;

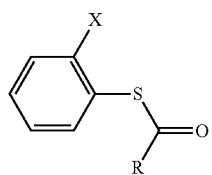

VII to obtain a compound of formula IV

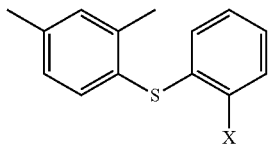

IV b) reacting the compound of formula IV with a compound of formula III in the presence of a base, a palladium catalyst, a ligand and a solvent;

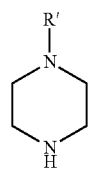

III wherein R' is hydrogen or protecting group; to obtain a of formula IB;

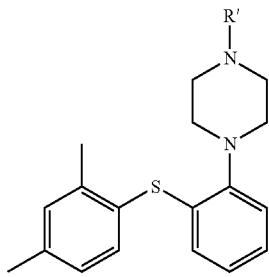

IB c) optionally the compound of formula IB is de-protected when R' is a protecting group, to obtain the compound of formula IA or a pharmaceutically acceptable salt thereof;

Method F:

a) reacting a compound of formula VII

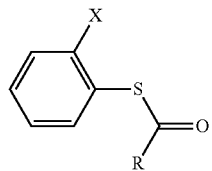

VII wherein R=hydrogen, alkyl or an aromatic group; with a compound of formula III in the presence of a base, a palladium catalyst, a ligand and a solvent;

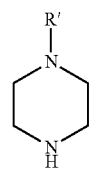

III wherein R' is hydrogen or a protecting group; to obtain a compound of formula VIII;

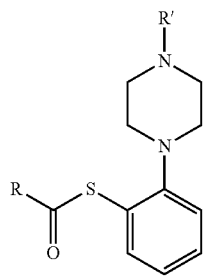

VIII b) reacting the compound of formula VIII with a compound of formula VI in the presence of a base, a palladium catalyst, a ligand and a solvent;

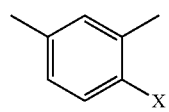

VI wherein X is a leaving group; to obtain a compound of formula IB;

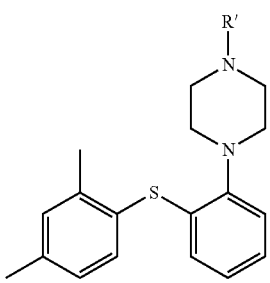

IB c) optionally the compound of formula IB is de-protected when R' is a protecting group, to obtain the compound of formula IA or a pharmaceutically acceptable salts thereof.

2. The process according to claim 1, wherein the solvent is an organic solvent selected from the group consisting of methylene chloride, ethylene dichloride, chloroform, carbon tetrachloride, n-pentane, n-hexane, n-heptane, cyclohexane, toluene, xylene, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, tetrahydrofuran, dioxane, diethyl ether, diisopropyl ether, monoglyme, diglyme, N,N-dimethylformamide, and N,N-dimethylacetamide, dimethylsulfoxide; or mixtures of at least two thereof.

3. The process according to claim 1, wherein the palladium catalyst is selected from the group consisting of Tris (dibenzylideneacetone) dipalladium ($Pd_2(dba)_3$), Bis (dibenzylideneacetone) palladium ($Pd(dba)_2$) and Palladium(II) acetate ($Pd(OAc)_2$).

4. The process according to claim 1, wherein the ligand is selected from the group consisting of racemic 2,2'-bis-diphenylphosphanyl-[1,1']binaphtalenyl (rac-BINAP), 1,1'-bis (diphenylphosphino) ferrocene (DPPF), bis-(2-diphenylphosphinophenyl)ether (DPEphos), tri-t-butyl phosphine (Fu's salt), biphenyl-2-yl-di-t-butyl-phosphine, (2'-dicyclohexylphosphanyl-biphenyl-2-yl)-dimethyl-amine, [2'-(di-t-butyl-phosphanyl)-biphenyl-2-yl]-dimethyl-amine, biphenyl-2-yl-dicyclohexyl-phosphine, and dicyclohexyl-(2',4',6'-tri-propyl-biphenyl-2-yl)-phosphane.

5. The process according to claim 1, wherein the base is selected from the group consisting of Sodium tert-butoxide (NaOt-Bu), Potassium tert-butoxide (KOt-Bu), 1,8-diazabicyclo[5.4.0]undec-7-ene (DBU), 1,4- diazabicyclo[2.2.2]octane (DABCO) and Caesium carbonate (Cs2CO3).

6. A process for the preparation of vortioxetine of formula IA,

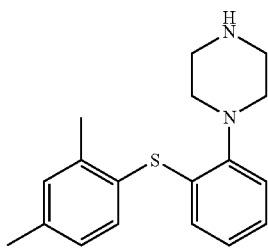

IA or a pharmaceutically acceptable salt thereof, comprising:
a) reacting the compound of formula

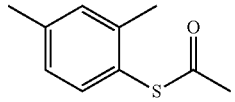

with

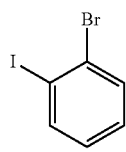

in the presence of a base, a palladium catalyst, a ligand and a solvent; to obtain the compound of formula

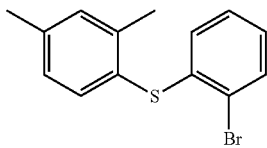 [SMILES: Cc1ccc(Sc2ccccc2Br)c(C)c1]

b) reacting the obtained product of step (a) with the compound of formula

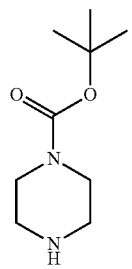

in the presence of a base, a palladium catalyst, a ligand and a solvent; to obtain the compound of formula IC

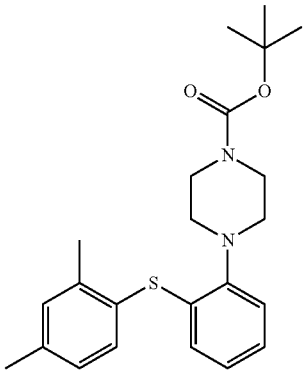

IC c) deprotecting the compound of formula IC with an aqueous acid to obtain vortioxetine or a pharmaceutically acceptable salt thereof.

7. The process according to claim 6 wherein the aqueous acid of step (c) is selected from the group consisting of HCl, HBr, $H_2SO_4$ and $H_3PO_4$.

* * * * *